(12) United States Patent
Havel (10) Patent No.: US 9,308,107 B2
(45) Date of Patent: Apr. 12, 2016

(54) ENDOLUMINAL PROSTHESIS AND DELIVERY DEVICE

(75) Inventor: William J. Havel, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 93 days.

(21) Appl. No.: 13/595,636

(22) Filed: Aug. 27, 2012

(65) Prior Publication Data

US 2014/0058402 A1 Feb. 27, 2014

(51) Int. Cl.
*A61F 2/06* (2013.01)
*A61F 2/954* (2013.01)
*A61F 2/966* (2013.01)

(52) U.S. Cl.
CPC ............... *A61F 2/954* (2013.01); *A61F 2/966* (2013.01); *A61F 2002/065* (2013.01); *A61F 2002/067* (2013.01)

(58) Field of Classification Search
CPC ............ A61F 2002/065; A61F 2002/067; A61F 2/954; A61F 2/95; A61F 2/962; A61F 2/966; A61F 2/97; A61F 2002/9505; A61F 2002/9528; A61F 2002/9534; A61F 2002/9665
USPC ........................ 623/1.23, 1.13, 1.35
See application file for complete search history.

(56) References Cited

U.S. PATENT DOCUMENTS

| | | | |
|---|---|---|---|
| 5,628,783 A | 5/1997 | Quiachon et al. ........... 623/1 |
| 5,676,697 A | 10/1997 | McDonald ................ 623/1 |
| 5,755,770 A * | 5/1998 | Ravenscroft ......... A61F 2/07 623/1.13 |
| 5,824,040 A * | 10/1998 | Cox .................... A61F 2/07 606/194 |
| 5,904,713 A | 5/1999 | Leschinsky ................ 623/1 |
| 6,334,867 B1 | 1/2002 | Anson ................... 623/1.13 |
| 6,551,350 B1 | 4/2003 | Thornton et al. ......... 623/1.13 |
| 6,576,009 B2 | 6/2003 | Ryan et al. ............. 623/1.35 |
| 6,645,242 B1 | 11/2003 | Quinn .................. 623/1.16 |
| 6,695,875 B2 | 2/2004 | Stelter et al. ........... 623/1.13 |
| 6,916,335 B2 | 7/2005 | Kanji ................... 623/1.11 |
| 7,014,653 B2 | 3/2006 | Ouriel et al. ........... 623/1.14 |
| 7,105,017 B2 * | 9/2006 | Kerr .................... A61F 2/07 623/1.13 |

(Continued)

FOREIGN PATENT DOCUMENTS

WO    WO 03/082153 A2    9/2003

OTHER PUBLICATIONS

Extended Search Report dated Nov. 21, 2013, for corresponding European Patent Application No. 13181872 (8 pages).

(Continued)

*Primary Examiner* — Jonathan W Miles
*Assistant Examiner* — Chima Igboko
(74) *Attorney, Agent, or Firm* — Brinks Gilson & Lione (57) ABSTRACT

A system for treating a body vessel may include a delivery device and a prosthesis retained on the delivery device. The prosthesis may include a main body and first and second legs each extending from the main body. The main body may include a lumen, and the first leg may include a lumen in fluid communication with the lumen of the main body. The second leg may include a tubular graft body and a stent attached to the graft body. The prosthesis may have a predeployment configuration in which the graft body of the second leg is inverted into and positioned within the lumen of the first leg, and the stent is positioned outside of the inverted graft body. The prosthesis may have a deployed configuration in which the second leg extends outward from the main body, and the stent is positioned within a lumen of the graft body.

19 Claims, 6 Drawing Sheets

(56) References Cited

U.S. PATENT DOCUMENTS

| | | | |
|---|---|---|---|
| 7,294,147 B2 | 11/2007 | Hartley | 623/1.13 |
| 7,435,253 B1 | 10/2008 | Hartley et al. | 623/1.12 |
| 7,537,606 B2 | 5/2009 | Hartley et al. | 623/1.11 |
| 7,645,298 B2* | 1/2010 | Hartley | A61F 2/07 623/1.13 |
| 7,678,141 B2* | 3/2010 | Greenan | A61F 2/07 623/1.13 |
| 8,226,706 B2* | 7/2012 | Hartley | A61F 2/07 623/1.11 |
| 8,273,115 B2* | 9/2012 | Hamer | A61F 2/07 623/1.11 |
| 8,979,892 B2* | 3/2015 | Shalev | A61F 2/90 606/213 |
| 2001/0012943 A1 | 8/2001 | Shaolian et al. | 606/108 |
| 2003/0199967 A1 | 10/2003 | Hartley et al. | 623/1.13 |
| 2003/0233140 A1 | 12/2003 | Hartley et al. | 623/1.11 |
| 2004/0073288 A1* | 4/2004 | Kerr | A61F 2/07 623/1.13 |
| 2004/0098084 A1 | 5/2004 | Hartley et al. | 623/1.11 |
| 2004/0215322 A1 | 10/2004 | Kerr | |
| 2006/0004433 A1 | 1/2006 | Greenberg et al. | 623/1.11 |
| 2007/0219614 A1 | 9/2007 | Hartley | 623/1.11 |
| 2007/0244547 A1* | 10/2007 | Greenan | A61F 2/07 623/1.35 |
| 2007/0250154 A1 | 10/2007 | Greenberg et al. | 623/1.13 |
| 2008/0114438 A1 | 5/2008 | Hartley et al. | 623/1.11 |
| 2009/0164001 A1* | 6/2009 | Biggs | A61F 2/07 623/1.35 |
| 2009/0248135 A1 | 10/2009 | Bruszewski et al. | 623/1.16 |
| 2009/0254170 A1* | 10/2009 | Hartley | A61F 2/07 623/1.12 |
| 2009/0264991 A1* | 10/2009 | Paul, Jr. | A61F 2/2418 623/1.35 |
| 2011/0054587 A1 | 3/2011 | Mayberry et al. | 623/1.11 |
| 2011/0054594 A1* | 3/2011 | Mayberry | A61F 2/07 623/1.34 |
| 2011/0066220 A1* | 3/2011 | Laguna | A61F 2/07 623/1.2 |
| 2011/0118763 A1* | 5/2011 | Beane | A61B 17/11 606/153 |
| 2012/0123527 A1 | 5/2012 | Isch | 623/1.35 |

OTHER PUBLICATIONS

Communication/Examination dated Jul. 16, 2015 for corresponding European Patent Application No. 13181872 (7 pages).

* cited by examiner

ENDOLUMINAL PROSTHESIS AND DELIVERY DEVICE

TECHNICAL FIELD

The present disclosure relates generally to medical devices. More particularly, it relates to an endoluminal prosthesis for implantation within a human or animal body for repair of damaged vessels, ducts, or other physiological pathways and systems and methods for delivering and deploying such an endoluminal prosthesis.

BACKGROUND

The functional vessels of human and animal bodies, such as blood vessels and ducts, occasionally weaken or even rupture. For example, the aortic wall can weaken, resulting in an aneurysm. Upon further exposure to hemodynamic forces, such an aneurysm can rupture. It has been found that in Western European and Australian men who are between 60 and 75 years of age, aortic aneurysms greater than 29 mm in diameter are present in 6.9% of the population, and those greater than 40 mm are present in 1.8% of the population.

One surgical intervention for weakened, aneurysmal, or ruptured vessels involves the use of a prosthetic device to provide some or all of the functionality of the original, healthy vessel, and/or preserve any remaining vascular integrity by replacing a length of the existing vessel wall that spans the site of vessel failure. For example, techniques have been developed for repairing abdominal aortic aneurysms by intraluminally delivering an endovascular graft to the aneurysm site through the use of a catheter-based delivery system. The endovascular grafts typically include a tube of pliable material (e.g., expanded polytetrafluoroethylene (ePTFE) or woven polyester) in combination with a graft anchoring component, which operates to hold the tubular graft in its intended position within the aorta. Most commonly, the graft anchoring component is formed of a stent or frame that is radially expandable to exert outwardly directing radial pressure against the surrounding blood vessel wall. The stent or frame can be either attached to or incorporated into the body of the tubular graft or provided separate from the graft and deployed within the graft.

It is preferable that these prostheses seal off the failed portion of the vessel. For weakened or aneurysmal vessels, even a small leak in the prosthesis may lead to the pressurization of, or flow in, the treated vessel which may aggravate the condition the prosthesis was intended to treat. A prosthesis of this type may be used, for example, to treat aneurysms of the abdominal aortic, iliac, or branch vessels, such as the renal, arteries.

A prosthetic device may be of unitary construction or may include multiple prosthetic modules. Modular systems typically are assembled in situ by overlapping the tubular ends of the prosthetic modules so that the end of one module sits partially inside the other module, preferably forming circumferential apposition through the overlap region. This attachment process is called "tromboning." The connections between prosthetic modules are typically maintained by the frictional forces at the overlap region and enhanced by the radial force exerted by the internal prosthetic module on the external prosthetic module where the two overlap. The fit may be further enhanced by stents fixed to the modules at the overlap region.

A prosthetic device including multiple prosthetic modules may be used for placement at a bifurcation or branch of the vasculature, In the case of a bifurcation, one module may be placed in the primary body vessel and one leg of the bifurcation, and another module may be placed in the other leg of the bifurcation. In the case of a branch, one module may be placed in the primary body vessel, and another module may be placed in the branch vessel. Multiple delivery devices may be used to place the different modules used to form the prosthetic device.

SUMMARY

The present embodiments provide an endoluminal prosthesis for implantation within a human or animal body for repair of damaged vessels, ducts, or other physiological pathways and systems and methods for delivering and deploying such an endoluminal prosthesis.

In one example, a system for treating a body vessel may include a delivery device and a prosthesis retained on the delivery device. The prosthesis may include a main body, a first leg extending from the main body, and a second leg extending from the main body. The main body may include a proximal end, a distal end, and a lumen extending from the proximal end to the distal end of the main body. The first leg may include a proximal end, a distal end, and a lumen extending from the proximal end to the distal end of the first leg and in fluid communication with the lumen of the main body. The second leg may include a tubular graft body including a proximal end and a distal end. The second leg may include a stent attached to the graft body. The prosthesis may have a predeployment configuration and a deployed configuration. In the predeployment configuration, the graft body of the second leg may be inverted into and positioned within the lumen of the first leg. In the predeployment configuration, the stent may be positioned outside of the inverted graft body of the second leg. In the deployed configuration, the second leg may extend outward from the main body, and the graft body of the second leg may include a lumen extending from the proximal end to the distal end of the graft body of the second leg and in fluid communication with the lumen of the main body. In the deployed configuration, the stent of the second leg may be positioned within the lumen of the graft body of the second leg.

In another example, a system for treating a body vessel may include a delivery device and a prosthesis retained on the delivery device in a predeployment configuration. The delivery device may include a primary delivery device and a secondary delivery device. The primary delivery device may include an elongate tubular primary sheath and an elongate tubular primary cannula received within a lumen of the primary sheath. The secondary delivery device may include an elongate tubular secondary sheath received within the lumen of the primary sheath and an elongate tubular secondary cannula received within a lumen of the secondary sheath. The prosthesis may include a main body, a first leg extending from the main body, and a second leg extending from the main body. The main body may include a proximal end, a distal end, and a lumen extending from the proximal end to the distal end of the main body. The first leg may include a proximal end, a distal end, and a lumen extending from the proximal end to the distal end of the first leg and in fluid communication with the lumen of the main body. The second leg may include a tubular graft body including a proximal end and a distal end. In the predeployment configuration, the graft body of the second leg may be inverted into and positioned within the lumen of the first leg. The prosthesis may be movable to a deployed configuration in which the second leg extends from the main body adjacent to the first leg. In the predeployment configuration, the primary cannula may be received within the lumen of each of the main body and the first leg of the prosthesis, and the prosthesis may be positioned within the lumen of the primary sheath.

In another example, a method for treating a body vessel may include introducing a prosthesis into the body vessel on a delivery device. The delivery device may include a tubular primary sheath. A tubular primary cannula may be received within a lumen of the primary sheath. A tubular secondary sheath may be received within the lumen of the primary sheath. A tubular secondary cannula may be received within a lumen of the secondary sheath. The prosthesis may include a tubular main body, a tubular first leg extending from a distal end of the main body, and a tubular second leg extending from the main body. The method may include retracting the primary sheath to at least partially deploy the main body and the first leg of the prosthesis. The method may include advancing the secondary cannula relative to the primary cannula to revert the second leg of the prosthesis from a predeployment configuration in which the second leg is inverted into and positioned within a lumen of the first leg to a deployed configuration in which the second leg extends outward from the main body.

Other systems, methods, features, and advantages of the invention will be, or will become, apparent to one with skill in the art upon examination of the following figures and detailed description. It is intended that all such additional systems, methods, features, and advantages be within the scope of the invention, and be encompassed by the following claims.

DETAILED DESCRIPTION OF THE DRAWINGS AND THE PRESENTLY PREFERRED EMBODIMENTS

The present disclosure relates to an endoluminal prosthesis for implantation within a human or animal body for repair of damaged vessels, ducts, or other physiological pathways and systems and methods for delivering and deploying such an endoluminal prosthesis.

In the present disclosure, the term "proximal" refers to a direction that is generally closest to the heart during a medical procedure, while the term "distal" refers to a direction that is farthest from the heart during a medical procedure.

Figure 1:
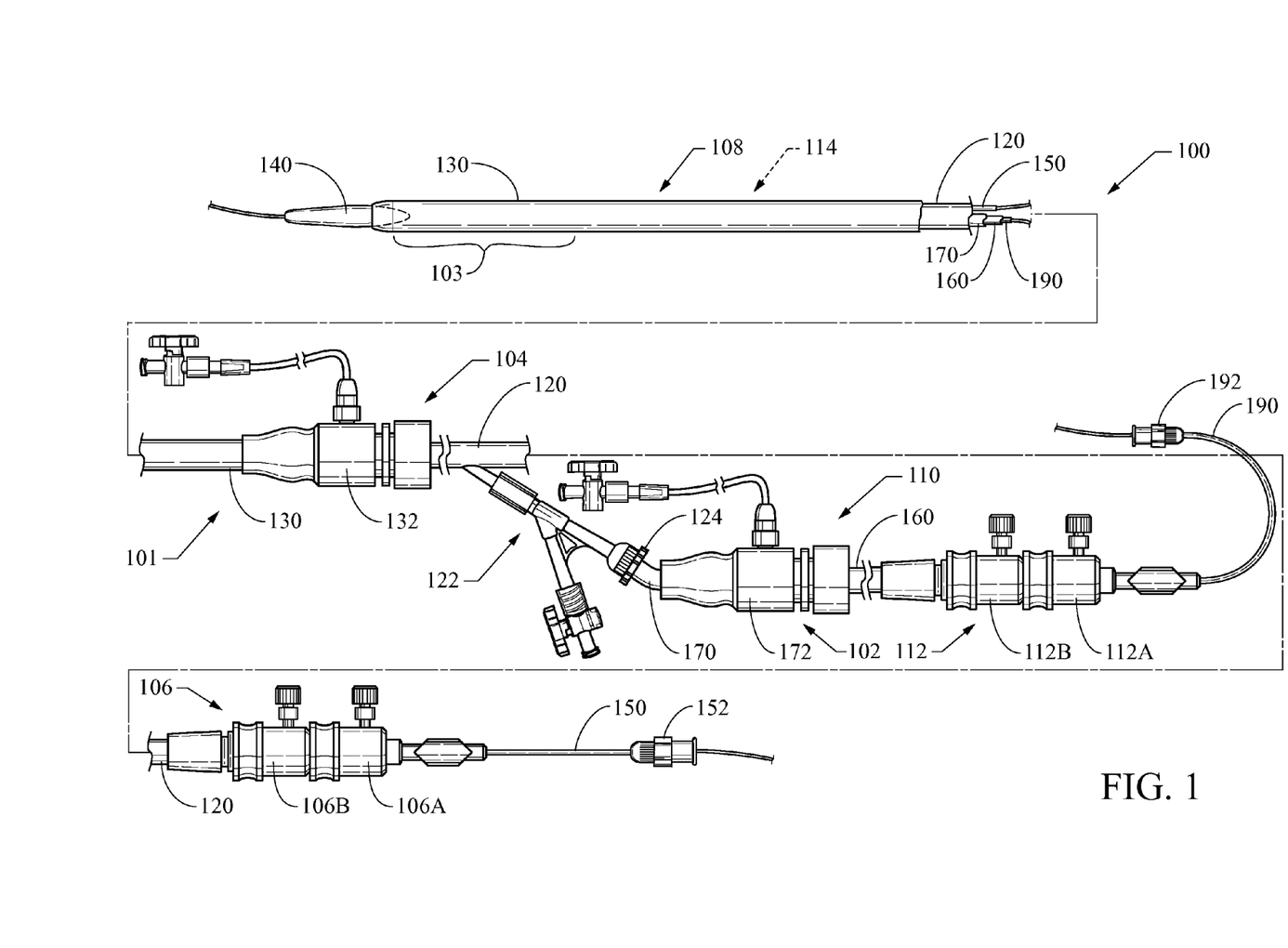
FIG. 1 illustrates one embodiment of a delivery device for deploying an endoluminal prosthesis.

FIG. 1 illustrates one example of a delivery device 100 in a condition for introduction of an endoluminal prosthesis into a patient. The delivery device 100 may include a primary delivery device 101 and a secondary delivery device 102. The primary delivery device 101 may be used to deliver an endoluminal prosthesis to a target location within a body vessel or a body lumen of a patient, and the secondary delivery device 102 may be received within the primary delivery device 101 to deploy a second leg of the prosthesis as further described below. The primary delivery device 101 may include a handle portion 104 and an introduction portion 108. The handle portion 104 may remain outside of the patient in use, and the introduction portion 108 may be introduced into the patient via a puncture in an artery such as a femoral artery. The primary delivery device 101 may include a catheter, such as the pusher catheter 120. The pusher catheter 120 may extend proximally from a trigger wire release region 106 of the handle 104. The pusher catheter 120 may be configured as an elongate tubular member having a lumen extending longitudinally therein. In one example, the pusher catheter 120 may include multiple lumens extending longitudinally therein as further described below with reference to FIGS. 4-5.

The primary delivery device 101 may include a sheath 130 and a sheath hub 132 extending over at least a portion of the pusher catheter 120. The sheath 130 may be configured as an elongate tubular member having a lumen extending longitudinally therein. The pusher catheter 120 may be slidably received within the lumen of the sheath 130. The sheath 130 may extend proximally from the sheath hub 132 to a nose cone 140 of the primary delivery device 101. The sheath 130 may be retracted relative to the pusher catheter 120 to at least partially expose a prosthesis retained below the sheath at a region 103 of the delivery device 100 located near the proximal end of the delivery device as further described below.

The primary delivery device 101 may include a guide wire cannula 150. The guide wire cannula 150 may extend from a connector 152 (e.g., a Luer lock hub) positioned at the distal end of the delivery device 100, through the handle 104 and the pusher catheter 120, and to the nose cone dilator 140. The guide wire cannula 150 may be configured as an elongate tubular member having a lumen extending longitudinally therein. The guide wire cannula 150 may be received within a lumen of the pusher catheter 120. The guide wire cannula 150 may extend at least partially through the nose cone 140. The guide wire cannula 150 may be tracked over a guide wire in a conventional manner to guide the delivery device 100 through the vasculature of the patient. The connector 152 may be used to introduce liquids such as contrast media to enable tracking of the progress of an operation.

The pusher catheter 120 may include a side arm 122 positioned proximal of the trigger wire release region 106 of the handle 104. In one example, the side arm 122 may be configured as a "Y" shaped extension extending outward away from the pusher catheter 120 as shown in FIG. 1. In other examples, the side arm 122 may have any other suitable configuration. The side arm 122 may be configured as a tubular member including a lumen extending longitudinally therein and in fluid communication with the lumen of the pusher catheter 120. The side arm 122 may include a seal 124 positioned at the distal end of the side arm. The secondary delivery device 102 may be introduced into the lumen of the pusher catheter 120 through the seal 124 and the side arm 122 as shown in FIG. 1.

The secondary delivery device 102 may include a handle portion 110 and an introduction portion 114. The handle portion 110 may remain outside of the patient in use, and the introduction portion 114 may be introduced into the patient via the pusher catheter 120 of the primary delivery device 101. The secondary delivery device 102 may include a catheter, such as the secondary pusher catheter 160. The secondary pusher catheter 160 may extend proximally from a trigger wire release region 112 of the handle 110. The secondary pusher catheter 160 may be configured as an elongate tubular member having a lumen extending longitudinally therein.

The secondary delivery device 102 may include a secondary sheath 170 and a secondary sheath hub 172 extending over at least a portion of the secondary pusher catheter 160. The secondary sheath 170 may be configured as an elongate tubular member having a lumen extending longitudinally therein. The secondary pusher catheter 160 may be slidably received within the lumen of the secondary sheath 170. The secondary sheath 170 may extend proximally from the secondary sheath hub 172 to a secondary nose cone 180 (shown in FIG. 4) of the secondary delivery device 102. The secondary sheath 170 may be retracted relative to the secondary pusher catheter 160 to expose a stent retained below the secondary sheath during deployment of the second leg of the prosthesis as further described below.

The secondary delivery device 102 may include a secondary guide wire cannula 190. The secondary guide wire cannula 190 may extend from a connector 192 (e.g., a Luer lock hub) positioned at the distal end of the delivery device 100, through the handle 110 and the secondary pusher catheter 160, and to the secondary nose cone 180. The secondary guide wire cannula 190 may be configured as an elongate tubular member having a lumen extending longitudinally therein. The secondary guide wire cannula 190 may be received within a lumen of the secondary pusher catheter 160. The secondary guide wire cannula 190 may extend at least partially through the secondary nose cone 180. The secondary guide wire cannula 190 may be tracked over a guide wire in a conventional manner to guide the secondary delivery device 102 into a body vessel (e.g., a contralateral iliac artery) as further described below. The connector 192 may be used to introduce liquids such as contrast media to enable tracking of the progress of an operation.

Figure 2:
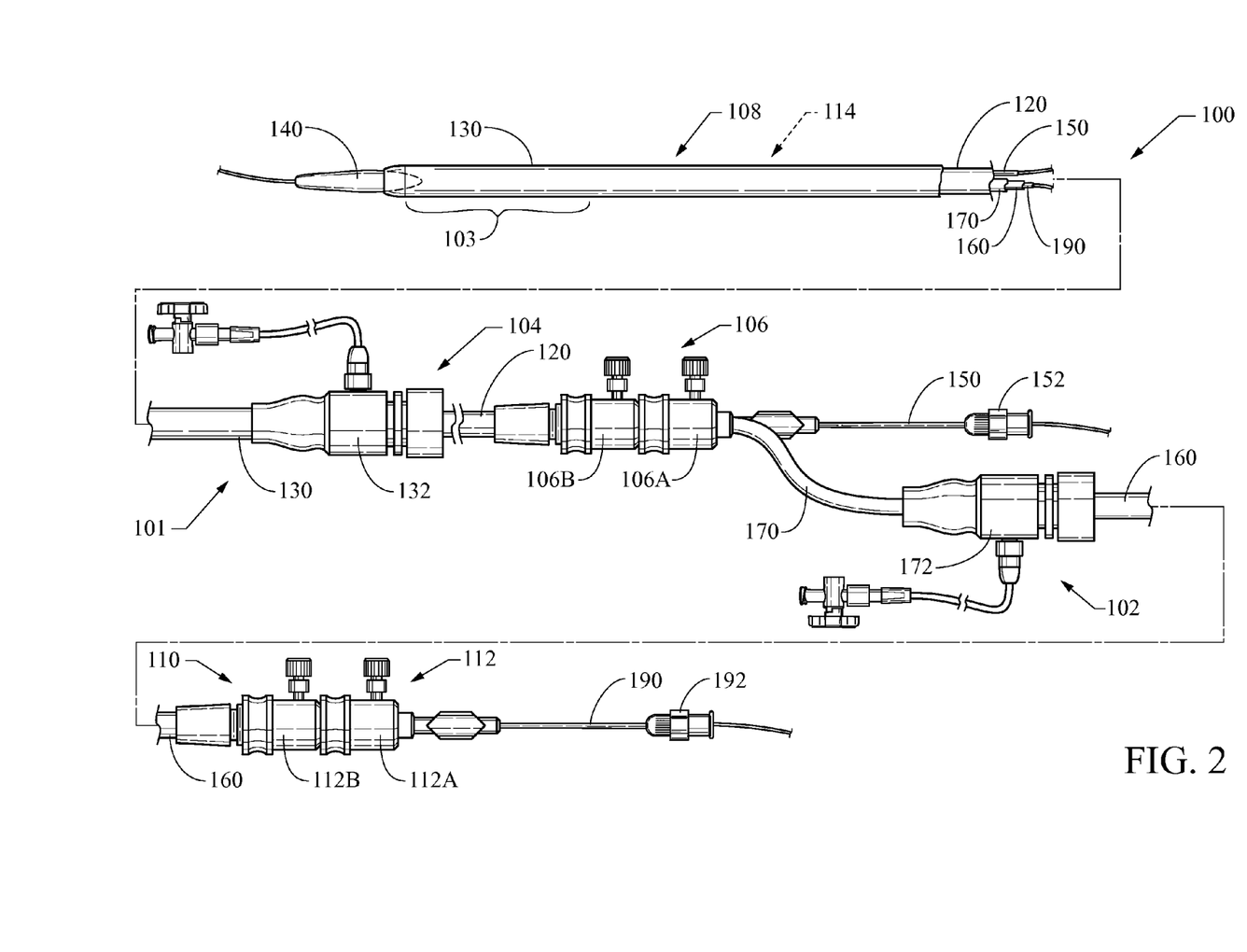
FIG. 2 illustrates another embodiment of a delivery device for deploying an endoluminal prosthesis.

FIG. 2 illustrates an alternative embodiment of the delivery device 100. The secondary delivery device 102 may enter the lumen of the pusher catheter 120 of the primary delivery device 101 at the distal end of the pusher catheter 120 near the trigger wire release region 106 of the primary delivery device as shown in FIG. 2. The pusher catheter 120 may include a seal positioned at the distal end of the lumen through which the secondary delivery device 102 may enter the pusher catheter 120. In this example, the primary delivery device may or may not include the side arm 122.

Figure 3:
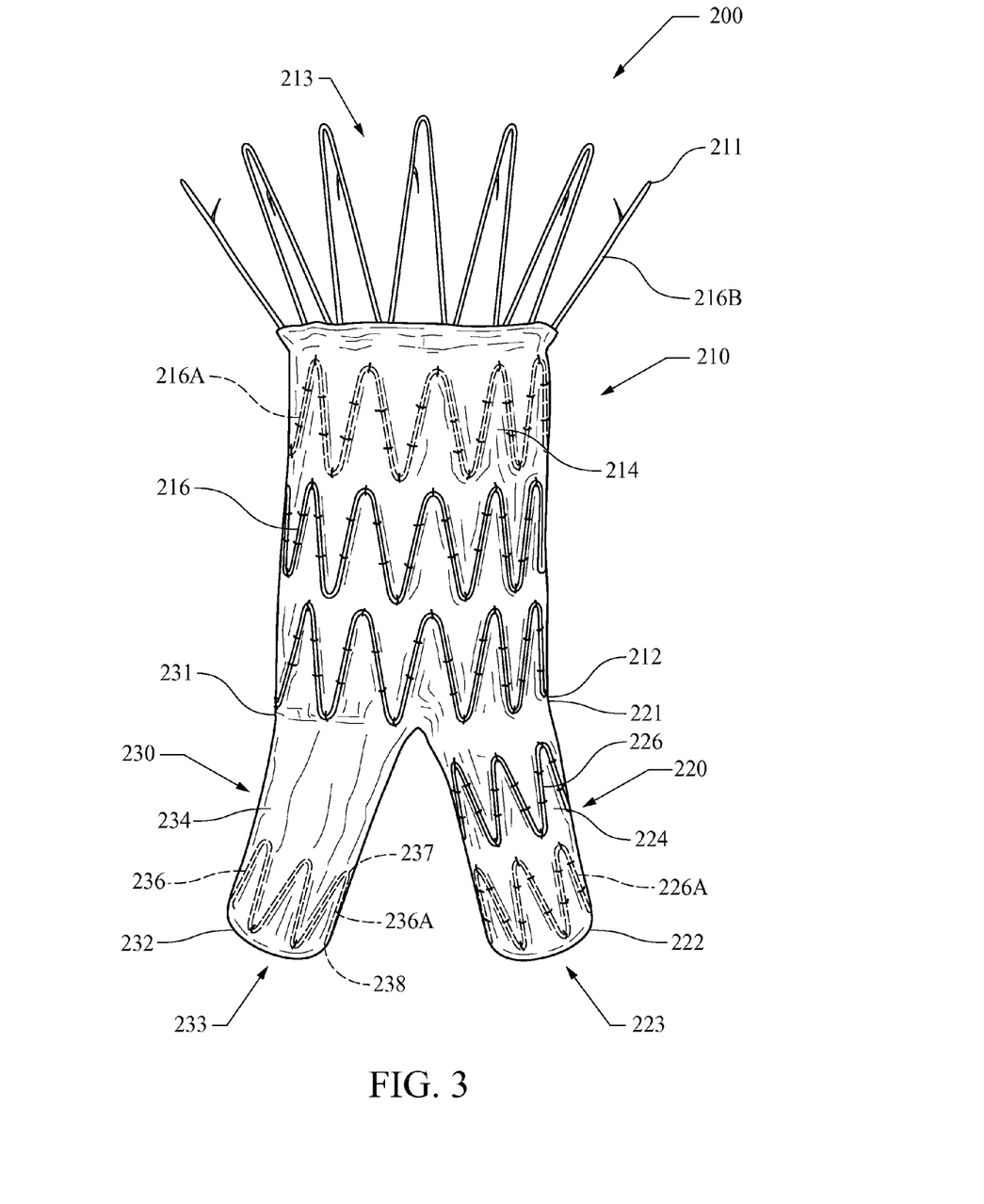
FIG. 3 illustrates one example of a bifurcated endoluminal prosthesis.

FIG. 3 shows one example of a prosthesis 200 that may be suitable for use with the delivery device 100. The prosthesis 200 may be configured for placement within a bifurcated body vessel (e.g., at an aortic bifurcation). To that end, the prosthesis 200 may include a main body 210, a first leg 220, and a second leg 230. In one example, the main body 210 may be configured for placement in the aorta; the first leg 220, or the ipsilateral leg, may be configured for placement in one iliac artery (e.g., an ipsilateral iliac artery); and the second leg 230, or the contralateral leg, may be configured for placement in another iliac artery (e.g., a contralateral iliac artery) as further described below. In other examples, the prosthesis may be configured for placement at any other bifurcation or branch within any other body vessel. For example, the prosthesis may be configured for placement at a bifurcation such as the bifurcation of the internal and external iliac arteries; at a branch such as the renal arteries, the innominate artery, or the subclavian artery; or any other bifurcation or branch at which multiple body vessels are joined to one another.

The main body 210 of the prosthesis 200 may have a proximal end 211, a distal end 212, and a lumen 213 extending longitudinally within the main body. The main body 210 may include a tubular graft body 214 of a biocompatible graft material. The graft body 214 may extend longitudinally along at least a portion of the length of the main body 210 to permit passage of blood or other body fluid within the main body. The main body 210 of the prosthesis 200 may include one or more stents 216 coupled to the graft body 214. The stents 216 may be conventional stents having any configuration known in the art as further described below. The stents 216 may be coupled to an internal surface of the graft body 214 or an external surface of the graft body. In one example, the main body 210 of the prosthesis 200 may include a sealing stent 216A coupled to the internal surface of the graft body 214 and positioned at or near the proximal end 211 of the main body. The sealing stent 216A may be positioned at the proximal end of the graft body 214 as shown in FIG. 3. The sealing stent 216A may aid in sealing the prosthesis 200 to a wall of a body vessel into which the prosthesis may be placed. Additionally, or alternatively, the main body 210 of the prosthesis 200 may include an attachment mechanism such as an attachment stent 216B positioned at the proximal end 211 of the main body. The attachment stent 216B may extend proximally beyond the proximal end of the graft body 214 as shown in FIG. 3. The attachment stent 216B may further secure the prosthesis 200 within the body vessel to prevent migration of the prosthesis within the body vessel. To that end, the attachment stent 216B may include one or more barbs which may be configured to engage the wall of the body vessel.

The first leg 220 of the prosthesis 200 may extend distally from the main body 210. The first leg 220 may have a proximal end 221, a distal end 222, and a lumen 223 extending longitudinally within the first leg. The first leg 220 may include a tubular graft body 224 of a biocompatible graft material. The graft body 224 may extend longitudinally along the length of the first leg 220 to permit passage of blood or other body fluid within the first leg. The graft body 224 of the first leg 220 may be attached to the graft body 214 of the main body 210 of the prosthesis 200. For example, the proximal end of the graft body 224 may be attached to the distal end of the graft body 214 as shown in FIG. 3. The lumen 223 of the first leg 220 may be in fluid communication with the lumen 213 of the main body 210 to permit passage of blood or other body fluid from the proximal end 211 of the main body to the distal end 222 of the first leg.

The first leg 220 of the prosthesis 200 may include one or more stents 226 coupled to the graft body 224. The stents 226 may be conventional stents having any configuration known in the art as further described below. The stents 226 may be coupled to an internal surface of the graft body 224 or an external surface of the graft body. In one example, the first leg 220 of the prosthesis 200 may include a sealing stent 226A coupled to the internal surface of the graft body 224 and positioned at or near the distal end 222 of the first leg as shown in FIG. 3. The sealing stent 226A may aid in sealing the prosthesis 200 to the wall of the body vessel.

The second leg 230 of the prosthesis 200 may extend distally from the main body 210. The second leg 230 may have a proximal end 231, a distal end 232, and a lumen 233 extending longitudinally within the second leg. The second leg 230 may include a tubular graft body 234 of a biocompatible graft material. The graft body 234 may extend longitudinally along the length of the second leg 230 to permit passage of blood or other body fluid within the second leg. The graft body 234 of the second leg 230 may be attached to the graft body 214 of the main body 210 of the prosthesis 200. For example, the proximal end of the graft body 234 may be attached to the distal end of the graft body 214 as shown in FIG. 3. The lumen 233 of the second leg 230 may be in fluid communication with the lumen 213 of the main body 210 to permit passage of blood or other body fluid from the proximal end 211 of the main body to the distal end 232 of the second leg.

The second leg 230 of the prosthesis 200 may include one or more stents 236 coupled to the graft body 234. The stents 236 may be conventional stents having any configuration known in the art as further described below. The stents 236 may be coupled to an internal surface of the graft body 234 or an external surface of the graft body. In one example, the second leg 230 of the prosthesis 200 may include a sealing stent 236A coupled to the internal surface of the graft body 234 and positioned at or near the distal end 232 of the second leg as shown in FIG. 3. The sealing stent 236A may aid in sealing the prosthesis 200 to the wall of the body vessel.

In one example, the second leg 230 of the prosthesis 200 may include a single stent, which may be the sealing stent 236A as shown in FIG. 3. The sealing stent 236A may extend longitudinally along a portion of the length of the second leg 230, and the remaining portion of the length of the second leg may be substantially free of stents or unstented. Alternatively, the sealing stent 236A may extend longitudinally along substantially the entire length of the second leg 230. The sealing stent 236A may include a first end 237 and a second end 238. The second end 238 of the sealing stent 236A may be attached to the graft body 234 (e.g., the internal surface of the graft body 234) at the distal end 232 of the second leg 230. The sealing stent 236A may be unattached to the graft body 234 except at the second end 238 of the sealing stent. In other words, the sealing stent 236A may include a single attachment point positioned at the second end 238 of the sealing stent and attached to the graft body 234 at the distal end 232 of the second leg 230. This may enable the second leg 230 of the prosthesis 200 to be inverted into the lumen 223 of the first leg 220 and the sealing stent 236A to be positioned substantially outside of the lumen 233 of the second leg for delivery into the body vessel as further described below. In one example, the sealing stent 236A may be configured as a bare stent (e.g., without an integral graft covering) attached to the distal end 232 of the second leg 230 as described herein. The sealing stent 236A may be expanded within the lumen 233 of the second leg 230 to support the graft body 234 of the second leg as further described below.

In one example, each of the first leg 220 and the second leg 230 of the prosthesis 200 may be attached to the main body 210. In this manner, the prosthesis 200 may be configured as a unitary structure defined by the main body 210, the first leg 220, and the second leg 230. In other words, the prosthesis 200 may be configured as a unibody stent graft. The first leg 220 and the second leg 230 of the prosthesis 200 may be attached to the main body 210 in any conventional manner. For example, the proximal end 221 of the graft body 224 of the first leg 220 and the proximal end 231 of the graft body 234 of the second leg 230 may be attached to the distal end 212 of the graft body 214 of the main body 210 by sutures, staples, clamps, adhesives, or any other suitable attachment mechanism. In one example, the graft body 224 of the first leg 220 and the graft body 234 of the second leg 230 may be attached to the graft body 214 of the main body 210 without the use of any extrinsic attachment mechanism. In other words, the graft bodies of the main body 210, the first leg 220, and the second leg 230 may be formed from a unitary graft material (e.g., a single piece of graft material).

The first leg 220 and the second leg 230 of the prosthesis 200 may be positioned adjacent to one another with each of the proximal end 221 of the first leg and the proximal end 231 of the second leg attached to the distal end 212 of the main body 210. The first leg 220 may extend from the main body 210 in a first direction to a first side of the main body, and the second leg 230 may extend from the main body in a second direction to a second side of the main body opposite the first side as shown in FIG. 3. In one example, the first leg 220 and the second leg 230 may extend from the main body 210 such that the prosthesis 200 is substantially "Y" shaped, with the first leg and the second leg forming the arms of the "Y" shape as shown in FIG. 3. In other words, the first leg 220 and the second leg 230 may extend away from the main body 210 and one another to form the arms of the "Y" shape. In this manner, the prosthesis 200 may be configured as a bifurcated prosthesis which may be configured for placement in a bifurcated body vessel as further described below. In one example, the proximal end 221 of the graft body 224 of the first leg 220 may be attached to the proximal end 231 of the graft body 234 of the second leg 230 (e.g., at the intersection of the two arms of the "Y" shape).

In another example, the prosthesis may be configured as a branched prosthesis. To that end, the proximal end of the first leg may extend from the distal end of the main body. The first leg may have a diameter that is substantially the same as the diameter of the main body. Additionally, or alternatively, the first leg and the main body may be coaxial with one another. The first leg and the main body may cooperatively define a unitary tubular body portion of the prosthesis. In other words, the prosthesis may include a tubular body portion having a proximal portion defined by the main body and a distal portion defined by the first leg. The body portion of the prosthesis may have a substantially cylindrical shape. In other words, the main body and the first leg may cooperatively define a substantially cylindrical main body portion. Alternatively, the main body portion may have any other suitable shape such as, for example, a tapering shape. The proximal end of the second leg may extend from an intermediate portion of the main body between the proximal end and the distal end of the main body. In other words, the second leg may be attached to a sidewall of the main body. The lumen of the second leg may be in fluid communication with the lumen of the main body through an aperture in the graft body of the main body. The second leg may define a tubular branch portion of the prosthesis extending from the body portion of the prosthesis. The second leg may extend from the main body at any suitable angle.

In any of the examples described herein, the main body 210, the first leg 220, and the second leg 230 may have any suitable dimensions (e.g., length or diameter). In one example, the main body 210 may have a length of between about 40 mm and about 200 mm, preferably between about 50 mm and about 120 mm, and/or a diameter of between about 14 mm and about 46 mm, preferably between about 18 mm and about 36 mm. Additionally, or alternatively, the first leg 220 may have a length of between about 40 mm and about 150 mm, preferably between about 60 mm and about 120 mm, and/or a diameter of between about 8 mm and about 28 mm, preferably between about 10 mm and about 24 mm. Additionally, or alternatively, the second leg 230 may have a length of between about 40 mm and about 150 mm, preferably between about 60 mm and about 120 mm, and/or a diameter of between about 8 mm and about 28 mm, preferably between about 10 mm and about 24 mm. The length of the first leg 220 may be substantially the same as the length of the second leg 230. Alternatively, the first leg 220 may have a longer or shorter length than the second leg 230.

In any of the examples described herein, the stents may have any suitable stent pattern known in the art. The stents may be balloon expandable. Preferably, the stents may be self-expandable. The stents may maintain the patency of the prosthesis and/or ensure adequate sealing against the surrounding vascular tissue. Any of the stents mentioned herein may include barbs and/or other anchoring members to help reduce the risk of prosthesis migration. One example of a stent pattern is the Z-stent or Gianturco stent design. Each Z-stent may include a series of substantially straight segments or struts interconnected by a series of bent segments or bends. The bent segments may include acute bends or apices. The Z-stents may be arranged in a zigzag configuration in which the straight segments are set at angles relative to one another and are connected by the bent segments. This design may provide both significant radial force as well as longitudinal support. In tortuous anatomy, branches, or fenestrations, it may be preferable to use alternative stents or modifications to the Z-stent design to avoid stent-to-stent contact. Alternative stent designs may include, for example, annular or helical stents.

The stents described herein may be made from any suitable material known in the art. In one example, the stents may be made from standard medical grade stainless steel and may be soldered using silver standard solder (0 lead/0 tin). In other examples, the stents may be made from a metallic material selected from any type of stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, a molybdenum alloy including about 0.4% to about 0.8% of lanthanum oxide ($La_2O_3$), a nickel-titanium alloy, or other suitable materials known in the art. The stents may be made from nitinol or other superelastic or shape-memory metal. Additionally, or alternatively, the stents may be configured in a variety of ways to provide a suitable intraluminal support structure. For example, one or more stents may be made from a woven wire structure, a laser-cut cannula, individual interconnected rings, or another pattern or design.

In any of the examples described herein, the graft bodies (e.g., the graft body 214 of the main body 210, the graft body 224 of the first leg 220, and/or the graft body 234 of the second leg 230) may be made of any material known in the art. The graft bodies may be made of the same or different materials. Preferably, the graft bodies may be formed from a biocompatible material that is substantially non-toxic in the in vivo environment of its intended use and substantially unrejected by the patient's physiological system (i.e., is non-antigenic). For example, the graft bodies may be made of an expanded polytetrafluoroethylene (ePTFE), polytetrafluoroethylene (PTFE), silicone, polyurethane, polyamide (nylon), polyethylene, polypropylene, polyaramid, polyacrylonitrile, cellulose, or another flexible biocompatible material. Additionally, or alternatively, the graft bodies may be formed from known fabric graft materials (e.g., woven polyester such as DACRON® from Invista (Wichita, Kans.), polyetherurethane such as THORALON® from Thoratec Corporation (Pleasanton, Calif.), or polyethylene such as an ultra-high molecular weight polyethylene (UHMwPE) such as DYNEEMA® from DSM Dyneema LLC (Stanley, N.C.)). Additionally, or alternatively, materials that are not inherently biocompatible may be subjected to surface modifications to render the materials biocompatible. Examples of surface modifications may include graft polymerization of a biocompatible polymer on the surface, coating of the surface with a crosslinked biocompatible polymer, chemical modification with a biocompatible functional group, or immobilization of a compatibilizing agent (e.g., heparin) or other biocompatible substance. Thus, any fibrous material having sufficient strength to survive in the in vivo environment may be used to form a textile graft, provided the final textile is biocompatible.

Additionally, or alternatively, the graft bodies may include a bioremodelable material such as reconstituted or naturally-derived collagenous materials. Suitable remodelable materials may be provided by collagenous extracellular matrix (ECM) materials possessing biotropic properties. For example, suitable collagenous materials may include ECM materials such as those including submucosa, renal capsule membrane, dermal collagen, dura mater, pericardium, fascia lata, serosa, peritoneum or basement membrane layers, including liver basement membrane. Suitable submucosa materials for these purposes may include, for example, intestinal submucosa including small intestinal submucosa, stomach submucosa, urinary bladder submucosa, and uterine submucosa. Collagenous matrices including submucosa (potentially along with other associated tissues) useful in the present invention may be obtained by harvesting such tissue sources and delaminating the submucosa-containing matrix from smooth muscle layers, mucosal layers, and/or other layers occurring in the tissue source. For additional information as to some of the materials which may be useful in the present invention, and their isolation and treatment, reference may be made, for example, to U.S. Pat. Nos. 4,902,508, 5,554,389, 5,993,844, 6,206,931, and 6,099,567. Non-limiting examples of suitable remodelable materials may include SURGISIS® BIODESIGN™ from Cook Medical (Bloomington, Ind.) or the graft prosthesis material described in U.S. Pat. No. 6,206,931 to Cook et al., which is incorporated herein by reference in its entirety. Additionally, or alternatively, the graft bodies may be made of any of the materials described in U.S. Pat. No. 7,407,509 to Greenberg et al. or U.S. Patent Application Pub. No. 2009/0171451 by Kuppurathanam et al., which are incorporated herein by reference in their entirety.

Figure 4:
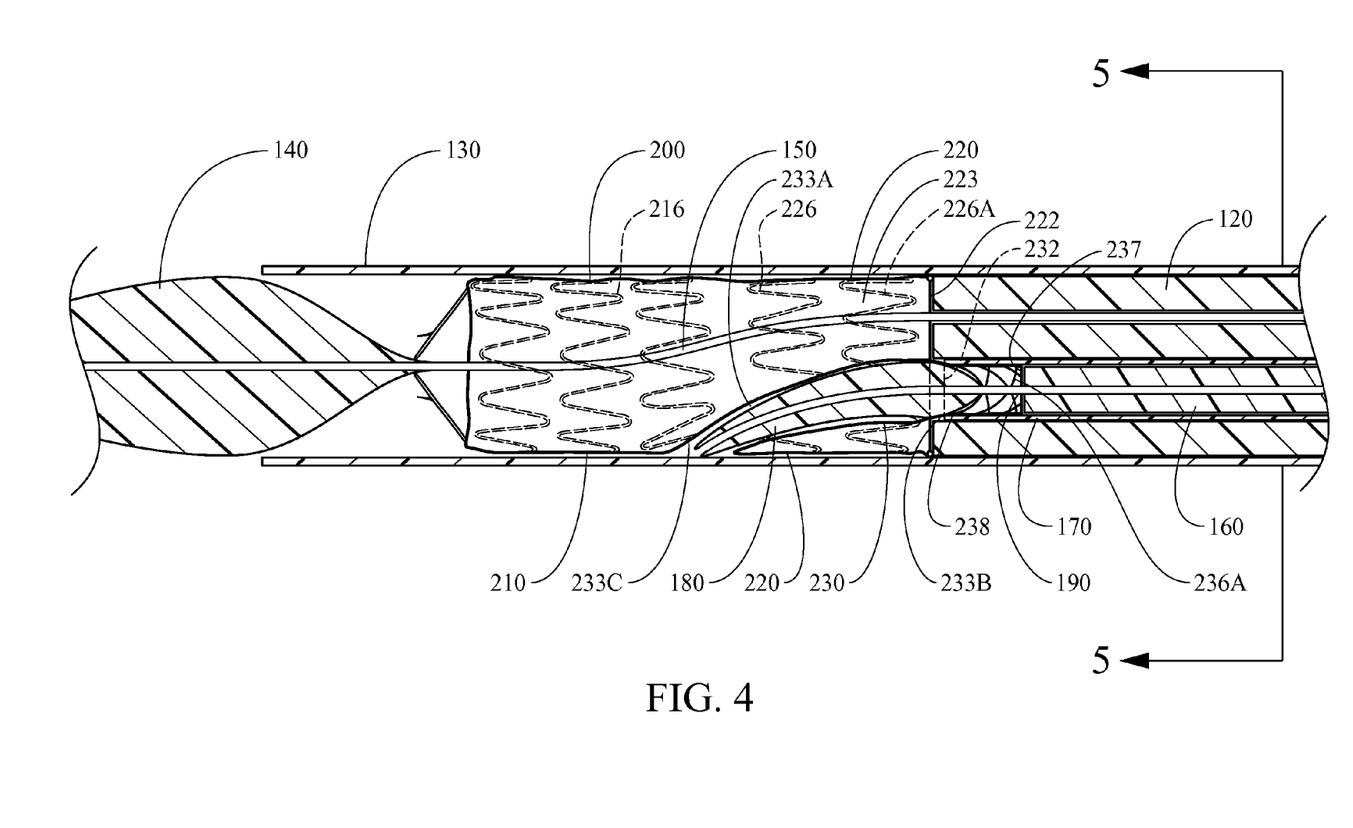
FIG. 4 is a longitudinal cross-sectional view of a proximal portion of the delivery device of FIG. 1 with the endoluminal prosthesis of FIG. 3 loaded thereon.
Figure 5:
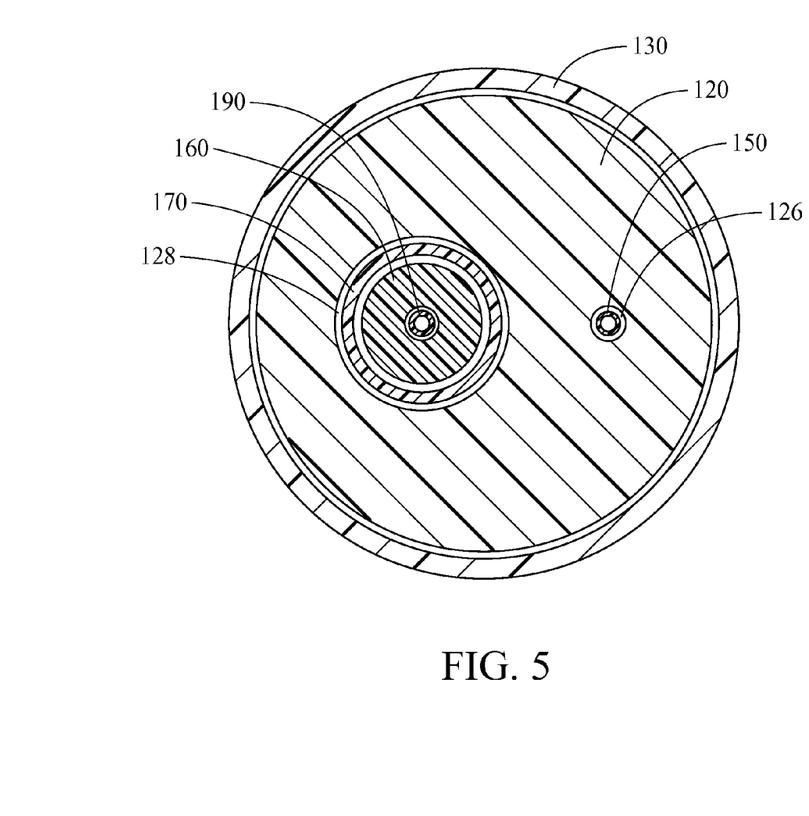
FIG. 5 is a transverse cross-sectional view of the delivery device of FIG. 1 taken along line 5-5 of FIG. 4.

FIG. 4 illustrates a longitudinal cross-sectional view of the region 103 of the delivery device 100 with the prosthesis 200 loaded thereon for introduction into a body vessel of a patient, and FIG. 5 illustrates a transverse cross-sectional view taken along line 5-5 of FIG. 4. The pusher catheter 120 of the primary delivery device 101 may be received within the sheath 130. In other words, a portion of the pusher catheter 120 may be positioned within the lumen of the sheath 130. The pusher catheter 120 may include a first lumen 126 and a second lumen 128 as best shown in FIG. 5. Each of the first lumen 126 and the second lumen 128 may extend longitudinally within the pusher catheter 120. The guide wire cannula 150 of the primary delivery device 101 may be received within the first lumen 126 of the pusher catheter 120. In other words, a portion of the guide wire cannula 150 may be positioned within the first lumen 126. Additionally, or alternatively, the secondary delivery device 102 may be received within the second lumen 128 of the pusher catheter 120. In other words, a portion of the secondary delivery device 102 may be positioned within the second lumen 128. For example, the secondary pusher catheter 160, the secondary sheath 170, and/or the secondary guide wire cannula 190 may be received within the second lumen 128 of the pusher catheter 120. In this manner, the secondary delivery device 102 may be preloaded into the primary delivery device 101 for introduction into the vasculature of the patient. The delivery device 100 may include a nested pair of delivery devices (e.g., the primary delivery device 101 and the secondary delivery device 102) within a single delivery sheath (e.g., the sheath 130). The secondary delivery device 102 may be slidably received within the lumen 128 such that the secondary delivery device may be longitudinally movable relative to the pusher catheter 120 of the primary delivery device 101 to deploy the second leg 230 of the prosthesis 200 as further described below. In another example, the pusher catheter 120 of the primary delivery device 101 may include a single lumen, and the guide wire cannula 150 and the secondary delivery device 102 may be positioned adjacent to one another within the single lumen of the pusher catheter 120. In another example, the secondary delivery device 102 may be positioned within the sheath 130 of the primary delivery device adjacent to the pusher catheter 120. In other words, the secondary delivery device 102 may be positioned outside of the lumen of the pusher catheter 120 and within the sheath 130.

The nose cone 140 of the primary delivery device 101 may be positioned proximal of the proximal end of the pusher catheter 120 as shown in FIG. 4. The guide wire cannula 150 may extend proximally beyond the proximal end of the pusher catheter 120 and to the nose cone 140. A longitudinal space may be formed between the proximal end of the pusher catheter 120 and the distal end of the nose cone 140. The prosthesis 200 may be positioned within the longitudinal space as further described below.

The secondary nose cone 180 of the secondary delivery device 102 may be positioned proximal of the proximal end of the secondary pusher catheter 160 as shown in FIG. 4. The secondary guide wire cannula 190 may extend proximally beyond the proximal end of the secondary pusher catheter 160 and to the secondary nose cone 180. A longitudinal space may be formed between the proximal end of the secondary pusher catheter 160 and the distal end of the secondary nose cone 180. The sealing stent 236A of the second leg 230 of the prosthesis 200 may be positioned within the longitudinal space as further described below.

The prosthesis 200 may be movable between a predeployment (i.e., loaded or delivery) configuration and a deployed configuration. FIG. 3 shows the prosthesis 200 in the deployed configuration, which is explained above. FIG. 4 shows the prosthesis 200 in the predeployment configuration. In the predeployment configuration, the second leg 230 of the prosthesis 200 may be inverted into the first leg 220 such that the second leg is positioned within the lumen 223 of the first leg. In one example, the length of the graft body 234 of the second leg 230 may be substantially equal to the length of the first leg 220. The distal end 232 of the graft body 234 of the inverted second leg 230 may be substantially longitudinally aligned with the distal end 222 of the first leg 220. In other examples, the length of the graft body of the second leg may be longer or shorter than the length of the first leg such that the distal ends of the graft bodies of the first and second legs may be longitudinally misaligned.

To invert the second leg 230, the distal end 232 of the graft body 234 may be rolled into the lumen 233 and pulled in a proximal direction within the lumen 233. This may cause the graft body 234 to roll in upon itself or to turn inside-out. As the second leg 230 is inverted, the sealing stent 236A may move proximally relative to the graft body 234 within the lumen 233. The sealing stent 236A may be unattached to the graft body 234 except at the distal end 238, which may enable such relative movement between the sealing stent 236A and the graft body 234. The sealing stent 236A may continue to move proximally relative to the graft body 234 until the second leg 230 is inverted and the sealing stent 236A is positioned outside of the graft body 234 of the second leg. In one example, the second leg 230 may be inverted by pulling the sealing stent 236A proximally relative to the graft body 234. The distal end 232 of the graft body 234, which may be attached to the second end 238 of the sealing stent 236A, may be pulled into the lumen 233 as the sealing stent 236A is moved proximally relative to the graft body 234. The sealing stent 236A may be pulled proximally until the sealing stent 236A is positioned outside of the second leg 230.

The inverted second leg 230 may be positioned within the lumen 223 of the first leg 220 of the prosthesis 200 as shown in FIG. 4. In other words, the inverted second leg 230 may be pulled distally into the lumen 223 of the first leg 220. The inverted second leg 230 may include a lumen 233A, which may be defined by an outer surface of the graft body 234. In other words, the graft body 234 may be turned inside-out such that the outer surface of the second leg 230 becomes the inner surface of the inverted second leg and defines the lumen 233A. The lumen 233A may include a first end opening 233B and a second end opening 233C as shown in FIG. 4. The sealing stent 236A may extend (e.g., distally) from the distal end 232 of the inverted second leg 230. In other words, the sealing stent 236A may be positioned distal of the distal end 232 of the inverted second leg 230 and substantially outside of the lumen 233A. The sealing stent 236A may be engaged by the secondary delivery device 102 to retain the sealing stent 236A in a reduced diameter configuration as further described below.

The prosthesis 200, in the predeployment configuration, may be loaded onto the delivery device 100 for introduction into the body vessel of the patient. The prosthesis 200 may be positioned within the sheath 130 of the primary delivery device 101. The main body 210 and the first leg 220 of the prosthesis 200 may be positioned longitudinally between the pusher catheter 120 and the nose cone 140 as shown in FIG. 4. The guide wire cannula 150 may be positioned within the lumen 213 of the main body 210 and the lumen 223 of the first leg 220 of the prosthesis 200. For example, the guide wire cannula 150 may exit the pusher catheter 120 and extend proximally through the lumen 223 of the first leg 220. The guide wire cannula 150 may extend further proximally through the lumen 213 of the main body 210 to the nose cone 140. In other words, the guide wire cannula 150 may extend within the prosthesis from the distal end 222 of the first branch 220 to the proximal end 211 of the main body 210.

The proximal end 211 of the main body 210 of the prosthesis 200 may be positioned at the distal end of the nose cone 140. The proximal end 211 of the main body 210 may be releasably attached to the primary delivery device 101 (e.g., the nose cone 140 or the guide wire cannula 150) in any conventional manner. For example, a trigger wire may be threaded through the attachment stent 216B and one or more apertures in the nose cone 140 and/or the guide wire cannula 150 to couple the proximal end 211 of the main body 210 to the primary delivery device 101. In this manner, the proximal end 211 of the main body 210 may be maintained in close proximity to the guide wire cannula 150. The trigger wire may extend distally to the trigger wire release region 106 of the primary delivery device 101. The trigger wire may be attached to a trigger wire release mechanism which may be retracted to release the trigger wire as further described below. The proximal end 211 of the main body 210 may be released to engage a wall of a body vessel as further described below.

Additionally, or alternatively, the distal end 222 of the first leg 220 may be releasably attached to the primary delivery device 101 (e.g., the pusher catheter 120 or the guide wire cannula 150) in any conventional manner. For example, a trigger wire may be threaded through the graft body 224 and/or the sealing stent 226A and one or more apertures in the pusher catheter 120 and/or the guide wire cannula 150 to couple the distal end 222 of the first leg 220 to the primary delivery device 101. In another example, a suture loop may be threaded through the graft body 224 and/or the sealing stent 226A, and the trigger wire may be threaded through the suture loop and one or more apertures in the pusher catheter 120 and/or the guide wire cannula 150. In this manner, the distal end 222 of the first leg 220 may be maintained in close proximity to the pusher catheter 120. The trigger wire may extend distally to the trigger wire release region 106 of the primary delivery device 101. The trigger wire may be attached to a trigger wire release mechanism which may be retracted to release the trigger wire as further described below. The distal end 222 of the first leg 220 may be released to engage a wall of a body vessel as further described below.

The prosthesis 200 may be compressed into a reduced diameter configuration in any conventional manner and positioned within the lumen of the sheath 130 as shown in FIG. 4. The sheath 130 may retain the prosthesis 200 in the reduced diameter configuration for delivery within the body vessel. For example, the main body 210 and/or the first leg 220 of the prosthesis 210 may be in contact with an inner surface of the sheath 130. The sheath 130 may prevent the stents 216 of the main body 210 and/or the stents 226 of the first leg 220 from expanding to an expanded configuration to retain the main body and/or the first leg in the reduced diameter configuration.

The second leg 230 of the prosthesis 200 may be engaged by the secondary delivery device 102. The sealing stent 236A of the second leg 230 may be positioned within the secondary sheath 170 of the secondary delivery device 102 and longitudinally between the secondary pusher catheter 160 and the secondary nose cone 180 as shown in FIG. 4. The sealing stent 236A may be compressed into a reduced diameter configuration in any conventional manner and positioned within the lumen of the secondary sheath 170. The secondary sheath 170 may retain the sealing stent 236A in the reduced diameter configuration for delivery within the body vessel. For example, the sealing stent 236A may be in contact with an inner surface of the secondary sheath 170. The secondary sheath 170 may prevent the sealing stent 236A from expanding to an expanded configuration.

The secondary guide wire cannula 190 may be positioned within a lumen of the sealing stent 236A of the second leg 230 of the prosthesis 200. For example, the secondary guide wire cannula 190 may exit the secondary pusher catheter 160 and extend proximally through the lumen of the sealing stent 236A to the secondary nose cone 180. The sealing stent 236A within the secondary sheath 170 may be positioned within the second lumen 128 of the pusher catheter 120 of the primary delivery device 101 as shown in FIG. 4. To that end, the proximal end of the secondary pusher catheter 160 may be positioned distal of the proximal end of the pusher catheter 120, and the sealing stent 236A may be positioned longitudinally between the proximal end of the secondary pusher catheter 160 and the proximal end of the pusher catheter 120. The secondary nose cone 180 of the secondary delivery device 102 may extend proximally beyond the proximal end of the pusher catheter 120 of the primary delivery device 101. The secondary nose cone 180 may be positioned within the lumen 233A of the inverted second leg 230 of the prosthesis 200. In other words, the graft body 234 of the second leg 230 may extend proximally beyond the secondary sheath 170 and over the secondary nose cone 180 as shown in FIG. 4.

The distal end 232 of the graft body 234 of the second leg 230 may be positioned at the distal end of the secondary nose cone 180. The distal end 232 of the graft body 234 of the second leg 230 may be releasably attached to the secondary delivery device 102 (e.g., the secondary nose cone 180 or the secondary guide wire cannula 190) in any conventional manner. For example, a trigger wire may be threaded through the graft body 234 and/or the second end 238 of the sealing stent 236A and one or more apertures in the secondary nose cone 180 and/or the guide wire cannula 190 to couple the distal end 232 of the graft body 234 of the second leg 230 to the secondary delivery device 102. The trigger wire may extend distally to the trigger wire release region 112 of the secondary delivery device 102. The trigger wire may be attached to a trigger wire release mechanism which may be retracted to release the trigger wire as further described below. Coupling the distal end 232 of the graft body 234 of the second leg 230 to the secondary delivery device may aid in controlling the second leg of the prosthesis 200 during deployment of the second leg as further described below.

Additionally, or alternatively, the first end 237 of the sealing stent 236A may be releasably attached to the secondary delivery device 102 (e.g., the secondary pusher catheter 160 or the secondary guide wire cannula 190) in any conventional manner. For example, a trigger wire may be threaded through the sealing stent 236A (e.g., at the first end 237) and one or more apertures in the secondary pusher catheter 160 and/or the secondary guide wire cannula 190 to couple the first end 237 of the sealing stent 236A to the secondary delivery device 102. The trigger wire may extend distally to the trigger wire release region 112 of the secondary delivery device 102. The trigger wire may be attached to a trigger wire release mechanism which may be retracted to release the trigger wire as further described below.

Figure 6:
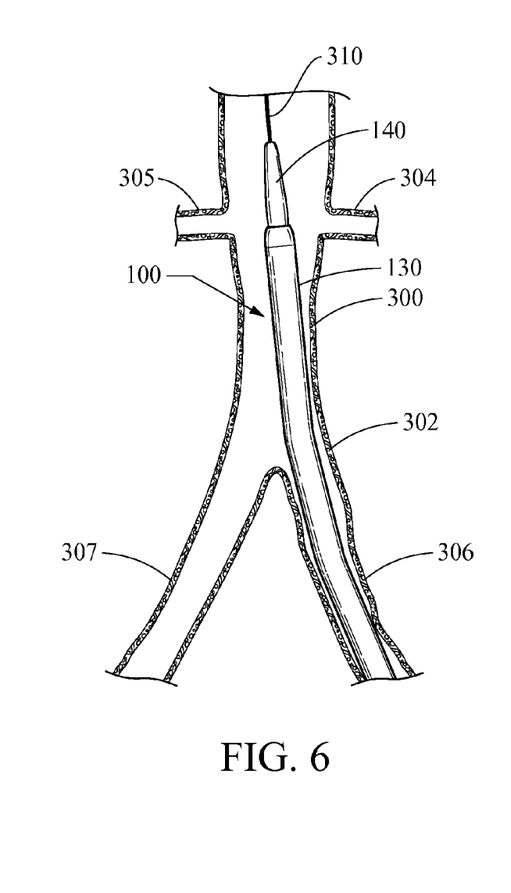
FIG. 6 illustrates introduction of the delivery device of FIG. 1 into an aorta of a patient.

FIGS. 6-9 illustrate exemplary method steps for deploying the prosthesis 200 within the vasculature of the patient using the delivery device 100. The vasculature may include an aorta 300 extending from a heart over a thoracic arch and distally to an aortic bifurcation 302. Proximal of the aortic bifurcation 302, a left renal artery 304 and a right renal artery 305 may extend from the aorta 300. At the aortic bifurcation 302, an ipsilateral iliac artery 306 and a contralateral iliac artery 307 may extend distally from the aortic bifurcation 302. Each of the ipsilateral iliac artery 306 and the contralateral iliac artery 307 may extend distally to a respective left or right femoral artery. A guide wire 310 may be introduced through a femoral puncture in a femoral artery (e.g., the left femoral artery) in a conventional manner. The guide wire 310 may be advanced proximally through the femoral artery into the ipsilateral iliac artery 306 and into the aorta 300. The guide wire 310 may be advanced proximally until the proximal end of the guide wire is positioned proximal of the renal arteries 304, 306 as shown in FIG. 6.

The delivery device 100 may be tracked over the guide wire 310 and into the aorta 300. For example, the guide wire 310 may be positioned within the guide wire cannula 150 of the primary delivery device 101. The delivery device 100 may be advanced proximally over the guide wire 310 until the proximal end 211 of the main body 210 of the prosthesis 200 is positioned just distal of the renal arteries 304, 304. Alternatively, the delivery device may be advanced proximally over the guide wire 310 until the proximal end 211 of the main body 210 is positioned just proximal of the renal arteries 304, 305. In this manner, the attachment stent 216B may span the ostia of the renal arteries 304, 305. In any case, the proximal end of the graft body 214 may be positioned distal of the renal arteries 304, 305 to avoid blocking blood flow to the renal arteries. The position of the prosthesis 200 may be visualized using any suitable visualization technique. To that end, the prosthesis 200 may include one or more radiopaque markers positioned at any longitudinal or circumferential position thereon (e.g., at the proximal end 211 of the main body 210 or the proximal end of the graft body 214) to aid in placing the prosthesis 200 within the aorta.

Figure 7:
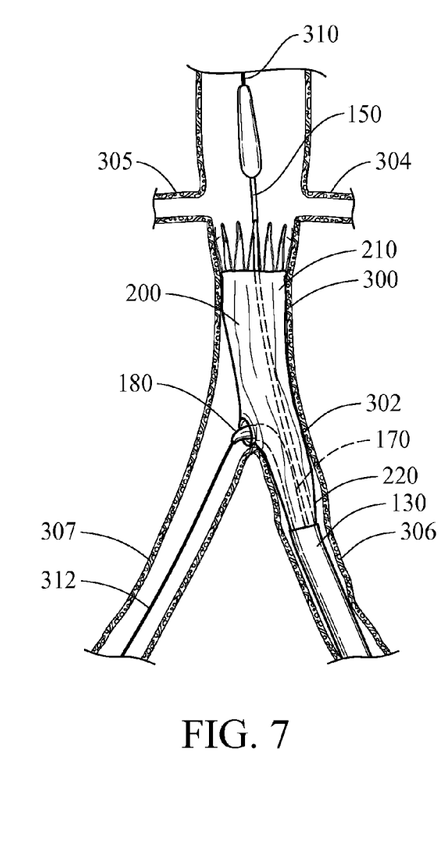
FIG. 7 illustrates deployment of a main body and an ipsilateral leg of the endoluminal prosthesis of FIG. 3 in an aorta of a patient.

The sheath 130 of the primary delivery device 101 may be retracted distally relative to the pusher catheter 120 to withdraw the sheath to at least partially expose the prosthesis 200 as shown in FIG. 7. The sheath 130 may be retracted a sufficient distance that the proximal end of the sheath 130 is positioned distal of the bifurcation point of the prosthesis 200. In this manner, the second end opening 233C of the lumen 233A of the inverted second leg 230 may be exposed for deployment of the second leg as further described below. Upon retraction of the sheath 130, the prosthesis may at least partially expand from the reduced diameter delivery configuration. For example, the main body 210 and the first leg 220 of the prosthesis 200 may at least partially expand from the reduced diameter delivery configuration. The second leg 230 of the prosthesis 200 may remain engaged by the secondary delivery device 102 such that the sealing stent 236A may remain in the reduced diameter delivery configuration within the secondary sheath 170 within the first leg 220. Portions of the main body 210 and/or the first leg 220 of the prosthesis 200 may be retained in a partially expanded configuration to enable repositioning of the prosthesis within the aorta 300 prior to complete expansion of the prosthesis. For example, the proximal end 211 of the main body 210 and/or the distal end 222 of the first leg 220 may remain releasably attached to the primary delivery device 101 as described above. This may prevent the prosthesis 200 from becoming fixed to the wall of the aorta 300 so that the prosthesis may be repositioned within the aorta prior to complete expansion of the prosthesis.

Figure 8:
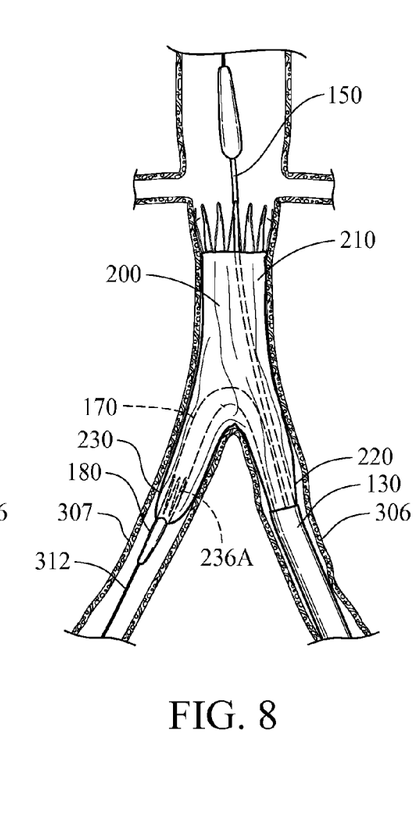
FIGS. 8-9 illustrate deployment of a contralateral leg of the endoluminal prosthesis of FIG. 3 in an aorta of a patient.

A secondary guide wire 312 may be advanced proximally within the secondary guide wire cannula 190 of the secondary delivery device 102. The secondary guide wire 312 may be advanced out through the end opening of the secondary nose cone 180 and into the contralateral iliac artery 307. The secondary guide wire 312 may be advanced distally within the contralateral iliac artery 307 as shown in FIG. 7. The secondary guide wire 312 may span the aortic bifurcation 302 such that a first portion of the secondary guide wire may be positioned within the ipsilateral iliac artery 306 and a second portion of the secondary guide wire may be positioned within the contralateral iliac artery 307. In one example, the secondary nose cone 180 may be curved as shown in FIGS. 4 and 7. For example, the secondary nose cone 180 may be curved in a direction toward the contralateral iliac artery 307 as shown in FIG. 7 to aid in guiding the secondary guide wire 312 into the contralateral iliac artery. The secondary delivery device 102 may be advanced proximally relative to the primary delivery device 101 and over the secondary guide wire 312. For example, the secondary pusher catheter 160, the secondary sheath 170, and the secondary guide wire cannula 190 may be advanced together relative to the pusher catheter 120 of the primary delivery device 101 within the second lumen 128. The secondary nose cone 180 may exit the lumen 233A of the inverted second leg 230 through the end opening 233C. The secondary nose cone 180 may be advanced into the contralateral iliac artery 307 and distally within the contralateral iliac artery over the second portion of the secondary guide wire 312 as shown in FIG. 8.

Advancing the secondary nose cone 180 over the second portion of the secondary guide wire 312 within the contralateral iliac artery 307 may cause the second leg 230 of the prosthesis 200 to revert from the predeployment configuration toward the deployed configuration. In other words, advancing the secondary nose cone 180 within the contralateral iliac artery 307 may turn the graft body 234 of the second leg 230 right-side-out. For example, the distal end 232 of the graft body 234 of the second leg 230 of the prosthesis 200 may be attached to the distal end of the secondary nose cone 180 as described above. As the secondary nose cone 180 is advanced distally within the contralateral iliac artery 307, the distal end 232 of the graft body 234 may be pulled distally within the lumen 233 of the second leg 230. The second end 238 of the sealing stent 236A, which may be attached to the distal end 232 of the graft body 234 of the second leg 230, may be pulled (or pushed, e.g., by the secondary pusher catheter 160) distally into the lumen 233 of the second leg. The secondary delivery device 102 may be advanced until the graft body 234 of the second leg 230 of the prosthesis 200 is fully reverted and the sealing stent 236A is positioned at the distal end 232 of the second leg (e.g., until the prosthesis is in the deployed configuration as shown in FIG. 3). When the secondary delivery device 102 is advanced into the contralateral iliac artery 307, the sealing stent 236A may become positioned within the reverted second leg 230.

Figure 9:
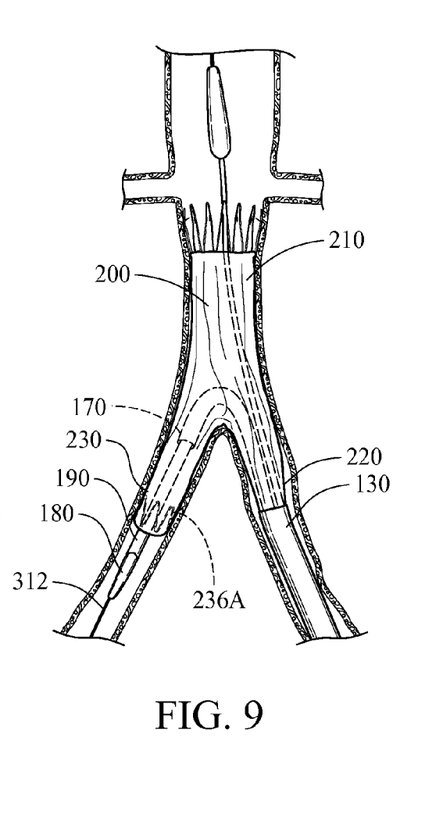

The secondary sheath 170 of the secondary delivery device 102 may be positioned within the lumen 233 of the second leg 230 and between the sealing stent 236A and the graft body 234. The sealing stent 236A may be retained in the reduced diameter delivery configuration within the secondary sheath 170. The secondary sheath 170 may be retracted relative to the secondary pusher catheter 160 to expose the sealing stent 236A within the lumen 233 of the second leg 230. Upon retraction of the secondary sheath 170, the sealing stent 236A may expand from the reduced diameter delivery configuration. The sealing stent 236A may expand to engage the inner surface of the graft body 234 of the second leg 230. In other words, the graft body 234 of the second leg 230 may be engaged between the sealing stent 236A and the wall of the contralateral iliac artery 307 as shown in FIG. 9. In this manner, the graft body 234 of the second leg may be sealed to the wall of the contralateral iliac artery 307.

The distal end 232 of the second leg 230 of the prosthesis 200 may be released from the secondary delivery device 102. For example, a first trigger wire release mechanism 112A positioned at the trigger wire release region 112 of the handle 110 of the secondary delivery device 102 may be retracted distally relative to the secondary pusher catheter 160. This may pull the trigger wire engaged with the distal end 232 of the second leg 230 as described above. The trigger wire release mechanism 112A may be pulled a sufficient distance to disengage the trigger wire from the distal end 232 of the second leg 230 to release the distal end of the second leg from the secondary delivery device 102.

Additionally, or alternatively, the first end 237 of the sealing stent 236A of the second leg 230 of the prosthesis 200 may be released from the secondary delivery device 102. For example, a second trigger wire release mechanism 112B positioned at the trigger wire release region 112 of the handle 110 of the secondary delivery device 102 may be retracted distally relative to the secondary pusher catheter 160. This may pull the trigger wire engaged with the first end 237 of the sealing stent 236A as described above. The trigger wire release mechanism 112B may be pulled a sufficient distance to disengage the trigger wire from the first end 237 of the sealing stent 236A to release the first end of the sealing stent from the secondary delivery device 102.

Additionally, or alternatively, the proximal end 211 of the main body 210 of the prosthesis 200 may be released from the primary delivery device 101. For example, a first trigger wire release mechanism 106A positioned at the trigger wire release region 106 of the handle 104 of the primary delivery device 101 may be retracted distally relative to the pusher catheter 120. This may pull the trigger wire engaged with the proximal end 211 of the main body 210 as described above. The trigger wire release mechanism 106A may be pulled a sufficient distance to disengage the trigger wire from the proximal end 211 of the main body 210 to release the proximal end of the main body from the primary delivery device 101. Upon release of the proximal end 211 of the main body 210, the attachment stent 216B may expand to engage the wall of the aorta 300. In this manner, the attachment stent 216B may be fixed to the wall of the aorta 300 to prevent migration of the prosthesis 200 within the aorta.

Additionally, or alternatively, the distal end 222 of the first leg 220 of the prosthesis 200 may be released from the primary delivery device 101. For example, a second trigger wire release mechanism 106B positioned at the trigger wire release region 106 of the handle 104 of the primary delivery device 101 may be retracted distally relative to the pusher catheter 120. This may pull the trigger wire engaged with the distal end 222 of the first leg 220 as described above. The trigger wire release mechanism 106B may be pulled a sufficient distance to disengage the trigger wire from the distal end 222 of the first leg 220 to release the distal end of the first leg from the primary delivery device 101.

With the prosthesis 200 fully released from the delivery device 100, the delivery device may be withdrawn from the patient's body. In one example, the secondary delivery device 102 may be retracted relative to the primary delivery device 101 until the secondary nose cone 180 of the secondary delivery device is positioned near or within the second lumen 128 of the pusher catheter 120. The primary delivery device 101 and the secondary delivery device 102 may be retracted together distally through the ipsilateral iliac artery 306 and out of the patient's body. Positioning the secondary nose cone 180 within the second lumen 128 of the pusher catheter 120 for withdrawal of the delivery device 100 may reduce the risk of catching or snagging the secondary nose cone on any portion of the prosthesis 200 during withdrawal of the delivery device. In another example, the secondary delivery device 102 may be retracted through the second lumen 128 of the pusher catheter 120 and withdrawn from the patient's body, leaving the primary delivery device 101 within the patient's body. The primary delivery device 101 may be withdrawn subsequent to the withdrawal of the secondary delivery device 102. In any of the examples described herein, the guide wire 310 and/or the secondary guide wire 312 may be withdrawn from the patient's body before, after, or during withdrawal of the delivery device 100.

Although use of the delivery device 100 has been described in relation to placement of a prosthesis at an aortic bifurcation, this disclosure is not so limited. The delivery device 100 may be used for the placement of any type of branched or bifurcated prosthesis at any branching or bifurcation point within a body vessel. For example, the delivery device 100 may be used to place a branched prosthesis at the renal arteries, the aortic arch branches (e.g., the innominate artery, the carotid artery, or the subclavian artery), other thoracic aorta branches (e.g., the celiac artery or the superior mesenteric artery), or any other branch at which multiple body vessels are joined to one another. Also for example, the delivery device 100 may be used to place a bifurcated prosthesis at the bifurcation of the internal and external iliac arteries, or at any other bifurcation at which multiple body vessels are joined to one another. Such alternatives are contemplated by and within the scope of this disclosure.

Use of a unibody stent graft, such as the prosthesis 200, may obviate the need for multiple prosthetic modules or reduce the number of modules which may be required to treat a condition in a body vessel. In one example, a procedure for treatment of a bifurcated body vessel may involve a single prosthesis or graft, without multiple modules. Reducing the number of modules used to form a prosthesis may reduce the risk of graft failure due to, for example, leakage at the joints between the modules or migration of the modules relative to one another.

Use of the delivery device 100, including the primary delivery device 101 and the secondary delivery device 102, may enable placement of the prosthesis 200 through a single insertion point (e.g., through a single femoral puncture). For example, it may be unnecessary to introduce a second instrument (e.g., a catheter and/or a snare) to aid in guiding the secondary guide wire 312 into the contralateral iliac artery 307. In one example, the prosthesis or graft may be implanted with a single, integrated delivery device without insertion of multiple devices during the procedure. This may reduce the time and/or complexity of a surgical procedure for placement of the prosthesis 200.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. A system for treating a body vessel, the system comprising:
   a delivery device and a prosthesis retained on the delivery device;
   the prosthesis comprising:
   a main body comprising a proximal end, a distal end, and a lumen extending from the proximal end to the distal end of the main body;
   a first leg extending from the distal end of the main body and comprising a proximal end, a distal end, and a lumen extending from the proximal end to the distal end of the first leg and in fluid communication with the lumen of the main body; and
   a second leg extending from the distal end of the main body and comprising a tubular graft body comprising a proximal end and a distal end, the second leg comprising a stent attached to the graft body;
   a predeployment configuration in which the graft body of the second leg is inverted into and positioned within the lumen of the first leg, and the stent of the second leg is positioned outside of the inverted graft body of the second leg; and
   a deployed configuration in which the second leg extends outward from the main body, the graft body of the second leg comprises a lumen extending from the proximal end to the distal end of the graft body of the second leg and in fluid communication with the lumen of the main body, and the stent of the second leg is positioned within the lumen of the graft body of the second leg,
   wherein the delivery device comprises a primary delivery device and a secondary delivery device;
   wherein the proximal end of the main body of the prosthesis is releasably attached to the primary delivery device, and a portion of the primary delivery device extends through the lumen of each of the first leg and the main body of the prosthesis; and
   wherein the distal end of the graft body of the second leg of the prosthesis is releasably attached to the secondary delivery device and a portion of the secondary delivery device is positioned within an inverted lumen of the second leg.

2. A system for treating a body vessel, the system comprising:
   a delivery device and a prosthesis retained on the delivery device;
   the prosthesis comprising:
   a main body comprising a proximal end, a distal end, and a lumen extending from the proximal end to the distal end of the main body;
   a first leg extending from the distal end of the main body and comprising a proximal end, a distal end, and a lumen extending from the proximal end to the distal end of the first leg and in fluid communication with the lumen of the main body; and
   a second leg extending from the distal end of the main body and comprising a tubular graft body comprising a proximal end and a distal end, the second leg comprising a stent attached to the graft body;
   a predeployment configuration in which the graft body of the second leg is inverted into and positioned within the lumen of the first leg, and the stent of the second leg is positioned outside of the inverted graft body of the second leg; and
   a deployed configuration in which the second leg extends outward from the main body, the graft body of the second leg comprises a lumen extending from the proximal end to the distal end of the graft body of the second leg and in fluid communication with the lumen of the main body, and the stent of the second leg is positioned within the lumen of the graft body of the second leg,
   wherein the delivery device comprises a primary delivery device comprising a tubular primary sheath and a tubular primary cannula, the primary cannula is positioned within the lumen of each of the first leg and the main body of the prosthesis, and the prosthesis is positioned within a lumen of the primary sheath.

3. The system of claim 2, wherein the stent of the second leg comprises a first end and a second end, the first end of the stent is unattached to the graft body of the second leg, and the second end of the stent is attached to the distal end of the graft body of the second leg.

4. The system of claim 2, wherein in the deployed configuration, the second leg extends from the main body adjacent to the first leg, and the first leg and the second leg cooperatively form a bifurcation of the prosthesis.

5. The system of claim 2, wherein the delivery device comprises a secondary delivery device comprising a tubular secondary sheath and a tubular secondary cannula; and
   wherein the stent of the second leg of the prosthesis comprises a first end and a second end attached to the distal end of the graft body of the second leg, and, in the predeployment configuration, the secondary cannula is positioned within a lumen of the stent of the second leg and the stent of the second leg is positioned distal of the distal end of the graft body of the second leg and within a lumen of the secondary sheath.

6. The system of claim 5, wherein the primary delivery device comprises a tubular primary catheter comprising a proximal end, a distal end, and a lumen extending longitudinally within the primary catheter, the primary catheter is positioned within the lumen of the primary sheath, the primary cannula is positioned within the lumen of the primary catheter, and each of the secondary sheath and the secondary cannula is positioned within the lumen of the primary catheter.

7. The system of claim 6, wherein the lumen of the primary catheter comprises a first lumen and a second lumen, the primary cannula is positioned within the first lumen, and each of the secondary sheath and the secondary cannula is positioned within the second lumen.

8. The system of claim 6, wherein the distal end of the first leg of the prosthesis is releasably attached to the proximal end of the primary catheter.

9. The system of claim 5, wherein the secondary delivery device comprises a tubular secondary catheter comprising a proximal end, a distal end, and a lumen extending longitudinally within the secondary catheter, the secondary catheter is positioned within the lumen of the secondary sheath, and the secondary cannula is positioned within the lumen of the secondary catheter.

10. The system of claim 9, wherein the first end of the stent of the second leg of the prosthesis is releasably attached to the proximal end of the secondary catheter.

11. A system for treating a body vessel, the system comprising:
    a delivery device and a prosthesis retained on the delivery device in a predeployment configuration;
    the delivery device comprising:
    a primary delivery device comprising an elongate tubular primary sheath and an elongate tubular primary cannula received within a lumen of the primary sheath; and
    a secondary delivery device comprising an elongate tubular secondary sheath received within the lumen of the primary sheath and an elongate tubular secondary cannula received within a lumen of the secondary sheath;
    the prosthesis comprising:
    a main body comprising a proximal end, a distal end, and a lumen extending from the proximal end to the distal end of the main body;
    a first leg extending from the distal end of the main body and comprising a proximal end, a distal end, and a lumen extending from the proximal end to the distal end of the first leg and in fluid communication with the lumen of the main body; and
    a second leg extending from the distal end of the main body and comprising a tubular graft body comprising a proximal end and a distal end;
    wherein, in the predeployment configuration, the graft body of the second leg is inverted into and positioned within the lumen of the first leg, and the prosthesis is movable to a deployed configuration in which the second leg extends from the main body adjacent to the first leg; and
    wherein, in the predeployment configuration, the primary cannula is received within the lumen of each of the main body and the first leg of the prosthesis, and the prosthesis is positioned within the lumen of the primary sheath.

12. The system of claim 11, wherein the distal end of the first leg of the prosthesis is releasably attached to the primary delivery device, and the distal end of the graft body of the second leg of the prosthesis is releasably attached to the secondary delivery device.

13. The system of claim 11, wherein the primary delivery device comprises an elongate tubular primary catheter comprising a proximal end, a distal end, and a lumen extending longitudinally within the primary catheter, the primary catheter is received within the lumen of the primary sheath, and the primary cannula is received within the lumen of the primary catheter.

14. The system of claim 13, wherein the distal end of the first leg of the prosthesis is releasably attached to the proximal end of the primary catheter.

15. The system of claim 11, wherein the second leg of the prosthesis comprises a stent comprising a first end that is unattached to the graft body of the second leg and a second end that is attached to the distal end of the graft body of the second leg, and, in the predeployment configuration, the stent of the second leg is positioned within the lumen of the secondary sheath.

16. The system of claim 15, wherein the secondary delivery device comprises an elongate tubular secondary catheter comprising a proximal end, a distal end, and a lumen extending longitudinally within the secondary catheter, the secondary catheter is received within the lumen of the secondary sheath, and the secondary cannula is received within the lumen of the secondary catheter.

17. The system of claim 16, wherein the first end of the stent of the second leg of the prosthesis is releasably attached to the proximal end of the secondary catheter.

18. The system of claim 11, wherein the secondary delivery device comprises a secondary nose cone attached to a proximal end of the secondary cannula, and, in the predeployment configuration, the secondary nose cone is positioned within an inverted lumen of the inverted second leg of the prosthesis.

19. A method for treating a body vessel, the method comprising:

introducing a prosthesis into the body vessel on a delivery device, the delivery device comprising a tubular primary sheath, a tubular primary cannula received within a lumen of the primary sheath, a tubular secondary sheath received within the lumen of the primary sheath, and a tubular secondary cannula received within a lumen of the secondary sheath, the prosthesis comprising a tubular main body, a tubular first leg extending from a distal end of the main body, and a tubular second leg extending from the distal end of the main body;

retracting the primary sheath to at least partially deploy the main body and the first leg of the prosthesis; and advancing the secondary cannula relative to the primary cannula to revert the second leg of the prosthesis from a predeployment configuration in which the second leg is inverted into and positioned within a lumen of the first leg to a deployed configuration in which the second leg extends outward from the main body.

* * * * *